(12) United States Patent
Hayashizaki et al.

(10) Patent No.: US 6,815,672 B2
(45) Date of Patent: Nov. 9, 2004

(54) METHOD OF ANALYZING POLYMER BY USING LASER ABRASION AND SYSTEM THEREFOR

(75) Inventors: Yoshihide Hayashizaki, Ibaraki (JP); Isao Tanihata, Saitama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 10/469,160

(22) PCT Filed: Feb. 22, 2002

(86) PCT No.: PCT/JP02/01594
§ 371 (c)(1),
(2), (4) Date: Oct. 27, 2003

(87) PCT Pub. No.: WO02/068952
PCT Pub. Date: Sep. 6, 2002

(65) Prior Publication Data
US 2004/0113606 A1 Jun. 17, 2004

(30) Foreign Application Priority Data
Feb. 27, 2001 (JP) .......................................... 2001-51919
Feb. 21, 2002 (JP) .......................................... 2002-44340

(51) Int. Cl.[7] ............................................. G01R 13/04
(52) U.S. Cl. ......................... 250/288; 250/281; 250/282
(58) Field of Search .......................... 427/569; 250/288, 250/281, 282

(56) References Cited
U.S. PATENT DOCUMENTS
2003/0129324 A1 * 7/2003 Genin et al. ................ 427/569

FOREIGN PATENT DOCUMENTS
| | | |
|---|---|---|
| JP | 62-284256 A | 12/1987 |
| JP | 10-74479 A | 3/1998 |
| JP | 2000-88809 A | 3/2001 |
| WO | WO 98/59360 A1 | 12/1998 |
| WO | WO 99/02728 A1 | 1/1999 |

OTHER PUBLICATIONS
Harada, Hideo, et al. 2000nen Ko Kagaku Toronkai Yoshishu, Hokkaido Daigaku Kogaku Kenkyuka Hen, Iwao Yamazaki, Nippon, Sep. 10, 2000, p. 288.

* cited by examiner

Primary Examiner—John R. Lee
Assistant Examiner—Erin-Michael Gill
(74) Attorney, Agent, or Firm—Birch, Stewart, Kolasch & Birch, LLP

(57) ABSTRACT

It becomes possible to simultaneously atomize and ionize atoms constituting a polymer with the use of a single laser, thereby highly simplifying the constitution of a system. A method of analyzing a polymer which comprises abrading the polymer to be analyzed by irradiating with laser beams to thereby atomize the polymer into the constituting elements thereof, then ionizing the elements and analyzing the constituting elements thus ionized. The laser beams with which the polymer to be analyzed is irradiated for the abrasion are ultrashort pulse laser beams. By irradiating the polymer with the ultrashort pulse laser beams to thereby abrade, the polymer can be atomized and ionized at the same time. Then the thus ionized constituting elements are analyzed.

28 Claims, 10 Drawing Sheets

| | SAMPLE1 | SAMPLE2 (dATP) |
|---|---|---|
| CHEMICAL FORMULA | $C_{42}H_{42}EuF_{21}O_6$ | $C_{10}H_{12}N_5O_{12}P_3Na_4$ |
| MOLECULAR WEIGHT | 1193 | 579 |
| SOLVENT | ETHANOL | WATER |
| CONCENTRATION | 0.7 mMol/l | 100 mMol/l |
| QUANTITY COATED | 0.0064(g) (AFTER DRYING) | 100($\mu$l) (BEFORE DRYING) |
| HEAT-RESISTANT TEMPERATURE | 150°C | −20°C    HALF YEAR<br>4°C    0.5% / month<br>20°C    5% / month<br>37°C    1% / day |
| MOLECULAR QUANTITY/SPOT | ~$2 \times 10^{14}$ | |
| OTHERS | SOLUTE: 5.5931(g)<br>SOLVENT:MIXED AT 5.6090(g) | |

SPECIFICATIONS OF TWO KINDS OF SAMPLES

MASS SPECTRUM

SAMPLE4 : 5-Chloro-2'-Deoxyuridine
CHEMICAL FORMULA : $C_9H_{11}ClN_2O_5$

METHOD OF ANALYZING POLYMER BY USING LASER ABRASION AND SYSTEM THEREFOR

This application is the national phase under 35 U.S.C. §371 of PCT International Application No. PCT/JP02/01594 which has an International filing date of Feb. 22, 2002, which designated the United States of America.

TECHNICAL FIELD

The present invention relates to a method of analyzing polymer using laser ablation and system therefor, more particularly to the method of analyzing polymer using laser ablation and system therefor, which are capable of significantly improving the efficiency of analysis comparing with a conventional ones, and the invention relates to the method of analyzing polymer using laser ablation and system therefor, which are preferably used in mass analysis of various kinds of polymer such as DNA, protein, RNA, PNA, lipid, sugar and the like, for example.

BACKGROUND ART

In recent years, the application range of the mass analysis has rapidly spread from the field of physics and chemistry to the field of life science such as medical science and biochemistry. Particularly, its development in decision calculus of protein molecular weight and decision calculus of amino-acid sequence is astonishing.

The principle of such mass analysis is that a sample is ionized by various kinds of method, ions obtained by ionization are separated according to mass/charge, and the intensity of each separated ion is measured.

Incidentally, conventional mass analysis for polymer has been the one that electron was added to the polymer itself to ionize it, its mass was analyzed or a molecule of high molecular weight was fragmented into molecular ions of low molecular weight to perform mass analysis, and constituent molecules were compared.

Herein, as an ion generating method in the conventional mass analysis of polymer, a secondary ion mass spectrometry (SIMS) where high-energy atomic ions are made to collide with polymer to cause ionization, an electron desorption ionization (ED) where the molecule is fragmented into the molecular ions of low molecular weight by electron impact, a matrix-assisted laser desorption ionization (MALDI), and the like are known, for example.

However, all of the above-described methods have had problems that they needed a mass spectrograph having high resolving power to perform mass analysis to polymeric ion and that the existence of fragment ions, which were decomposed/generated halfway, made the analysis of mass spectrum difficult.

On the other hand, as mass analysis method for a polymer sample labeled by isotope in performing chemical analysis, a laser atomization resonance ionization microprobe (LARIMP) where a nano-second laser performs atomization and ionization has been conventionally known.

However, according to the LARIMP method, two lasers that are an atomization laser to atomize a labeled element and a resonance ionization laser to ionize the atoms of the atomized labeled element are required as the laser, there has been a problem that the system configuration became complicate.

Moreover, resonance ionization needs to be performed to the labeled atoms in the LARIMP method as described above. For this reason, it is necessary to irradiate laser beams having a unique wavelength to each labeled atom, and there has been a problem that it was quite difficult to perform efficient analysis in the case where various kinds of labeled isotope were mixed.

The present invention has been invented in consideration of the various kinds of above-described problems that the prior art has, and its object is to provide the method of analyzing polymer using laser ablation and system therefor, which generate the atomic ions of constituent atoms that constitute polymer and analyze the generated atomic ions, and the mass analysis method for polymer using laser ablation and system therefor, which do not require a spectrograph of high resolving power. More specifically, the object is to provide the mass analysis method for polymer using laser ablation and system therefor, which eliminate a chance where the analysis of mass spectrum becomes difficult and where the mass spectrograph does not require high resolving power, in the case of performing mass analysis, for example.

Further, the object of the present invention is to provide the method of analyzing polymer using laser ablation and system therefor, which enables single laser to simultaneously realize atomization and ionization of the constituent atoms that constitute polymer, and to drastically simplify the system configuration.

Furthermore, the object of the present invention is to provide the method of analyzing polymer using laser ablation and system therefor, which are capable of performing efficient analysis even in the state where various kinds of labeled isotope are mixed.

DISCLOSURE OF INVENTION

To achieve the above-described objects, the present invention is one that the ultra-short pulse laser beams perform ablation to various kinds of polymers such as DNA, protein, RNA, PNA, lipid, sugar and the like, for example, the polymers are transferred into atomic ions to generate atomic ions, and the generated atomic ions are analyzed. With this configuration, the chemical analysis for various kinds of polymers can be performed.

Specifically, according to the present invention, by performing laser ablation to polymer by the ultra-short pulse laser beams, the polymer is decomposed in pieces and atomized by each of atoms that constitute the polymer, and the atomized atoms are ionized into univalent ions, and quantitative analysis can be performed by analyzing the atomic ions generated by the ionization.

Therefore, when performing mass analysis in the present invention, mass analysis is performed to the atomic ions of low mass, which eliminates the chance where the analysis of mass spectrum becomes difficult. The mass spectrograph does not require high resolving power.

Further, as described above, according to the present invention, by performing ablation to polymer by the ultra-short pulse laser, the ionization of atomized atoms into univalent ions can be efficiently performed simultaneously with the atomization of polymer. Therefore, the system configuration can be simplified, various kinds of labeled elements can be simultaneously used in performing chemical analysis, and thus analysis efficiency can be improved.

In the present invention, since the single ultra-short pulse laser can simultaneously atomize and ionize labeled elements, the system configuration can be drastically simplified.

Moreover, since the above-described ionization is ionization (non-resonance ionization) performed by high peak power intensity of the ultra-short pulse laser beams via non-resonant process, each labeled atom can be ionized even in the state where various kinds of labeled isotopes are mixed, it can be easily applied to a multi-label system, and highly accurate and highly efficient polymeric analysis can be performed.

Thus, the present invention is extremely preferable for the use in the quantitative analysis for gene expression, which will be increasingly important in future.

Specifically, the present invention is the method of analyzing polymer using laser ablation, where polymer is atomized into constituent elements by irradiating laser beams on the polymer, which is the analyzing subject, to perform ablation to the polymer, the atomized constituent elements are ionized, and the ionized constituent elements are thus analyzed, wherein the laser beams irradiated on the polymer, which is the analyzing subject, to perform ablation to the polymer are the ultra-short pulse laser beams, in which the polymer is simultaneously atomized into constituent elements and ionized by irradiating the ultra-short pulse laser beams on the polymer, which is the analyzing subject, to perform ablation to the polymer, and the ionized constituent elements are analyzed.

Herein, mass analysis can be cited as the above-described analysis, for example, and chemical analysis (so-called regular chemical analysis) or optical analysis (such as a fluorescence method), for example, is cited as analysis other than the mass analysis.

Further, in the present invention, the polymer that is the analyzing subject may be one transformed into solid phase (dry phase).

Furthermore, in the present invention, a method of transforming polymer into solid phase may be a method that includes a process of transforming the polymer into solid phase by dropping solution of the polymer, which is the analyzing subject, onto a substrate to dry.

Still further, in the present invention, the above-described substrate is a solid and the thermal conductivity of the solid may be 0.1 $W.m^{-1}.K^{-1}$ or more In addition, in the present invention, the polymer that is the analyzing subject may be the one added with an elemental label.

Further, in the present invention, the above-described elemental label may be a group 1 element in the periodic table.

Further, in the present invention, the above-described elemental label may be a group 16 element in the periodic table.

Further, in the present invention, the above-described elemental label may be a group 17 element in the periodic table.

Further, in the present invention, the above-described elemental label may be a transition metal element in the periodic table.

Further, in the present invention, the above-described element label may be a stable isotopic label.

Furthermore, in the present invention, the ultra-short pulse laser beams irradiated on the polymer, which is the analyzing subject, to perform ablation to the polymer may have a pulse duration of 10 pico seconds or less and a peak power of 10 megawatt or more.

Furthermore, in the present invention, the ultra-short pulse laser beams irradiated on the polymer, which is the analyzing subject, to perform ablation to the polymer may have the pulse duration of 1 femto second or more and 1 pico second or less, and the peak power of 1 gigawatt or more and 10 gigawatt or less.

Further, in the present invention, the analysis of the above-described ionized constituent element may be mass analysis.

Further, in the present invention, the mass analysis may be mass analysis by a time-of-flight method.

Furthermore, in the present invention, analysis may be simultaneously performed to a plurality of ionized constituent elements.

Still further, in the present invention, the polymer that is the analyzing subject may be nucleic acid or the analog of nucleic acid, which is fixed on a DNA microarray.

It is to be noted that DNA, RNA and PNA, for example, are specifically cited as the nucleic acid or the analog of nucleic acid.

Further, in the present invention, the above-described DNA microarray may be a multi-channel DNA microarray.

Further, in the present invention, by moving at least either one of the short pulse laser beams that perform ablation to polymer and the polymer that is the analyzing subject, the short pulse laser beams that perform ablation to the polymer may perform ablation to the polymer, which is the analyzing subject, without omission and duplication.

Furthermore, the present invention is an analysis system for polymer using laser ablation, where polymer is atomized into constituent elements by irradiating laser beams on the polymer, which is the analyzing subject, to perform ablation to the polymer, the atomized constituent elements are thus ionized, and the ionized constituent elements are analyzed, in which the system has a vacuum chamber capable of arranging a target inside thereof, a spectrograph arranged in the vacuum chamber, and an ultra-short pulse laser that emits ultra-short pulse laser beams to irradiate the target arranged in the above-described vacuum chamber.

Further, in the present invention, the system may further have moving means that moves the target in the above-described vacuum chamber.

Further, in the present invention, the moving means that moves the above-described target may be rotational means that rotates the target.

Moreover, in the present invention, the system may further have moving means that moves the irradiation position of the ultra-short pulse laser beams to the target.

Further, in the present invention, the above-described spectrograph may be a mass spectrograph.

Further, in the present invention, the above-described mass spectrograph may be a quadrupole mass spectrograph.

Still further, in the present invention, the above-described mass spectrograph may be a time-of-flight mass spectrograph.

Further, in the present invention, the above-described mass spectrograph may be a Fourier transform mass spectrograph of ion cyclotron type.

Furthermore, in the present invention, the above-described ultra-short pulse laser may irradiate short pulse laser beams having a pulse duration of 10 pico seconds or less and a peak power of 10 megawatt or more.

Still further, in the present invention, the above-described ultra-short pulse laser may irradiate short pulse laser beams having the pulse duration of 1 femto second or more and 1 pico second or less and the peak power of 1 gigawatt or more and 10 gigawatt or less.

Herein, in performing ablation to polymer by ultra-short pulse laser beams in the present invention, irradiating one shot (one pulse) of ultra-short pulse laser beams to polymer is enough. However, plural shots (plural pulses) of ultra-short pulse laser beams may be irradiated on polymer, and the shot number (pulse number) of ultra-short pulse laser beams irradiated on polymer may be appropriately selected.

In addition, it is preferable that the ultra-short pulse laser has the pulse duration of 10 pico seconds or less, and particularly, it is adequate to use laser of 1 femto second or more and 1 pico second or less, which is regularly referred to as femto second laser. As its peak power, 10 megawatt or more is preferable, and more specifically, 1 gigawatt or more and 10 gigawatt or less is preferable.

This is because multivalent ions are generated to make the analysis of mass spectrum difficult if the output is larger than the above-described range, and the efficiency of atomization/ionization reduces and it becomes impossible to observe an atomic ion signal if the output is smaller than the above-described range.

It is to be noted that, according to an experiment conducted by the inventor, which is described later, it was possible to obtain an excellent result in the case of the pulse duration of 110 femto seconds and the peak power of 2 gigawatt, for example.

Furthermore, according to the present invention, ultra-short pulse laser beams such as the femto second laser beams capable of efficiently performing atomization and ionization simultaneously is made to irradiate on a polymer sample that is labeled by isotope. For this reason, it is not necessary to selectively ionize the labeled elements and various kinds of labeled element can be used. Moreover, since the repetition rate of laser irradiation can be raised to a few kHz, the invention is suitable for high-speed analysis.

Further, in the present invention, by moving at least either one of the short pulse laser beams that perform ablation to polymer and the polymer that is the analyzing subject, the short pulse laser beams that perform ablation to the polymer perform ablation and analysis to the polymer, which is the analyzing subject, without omission and duplication. Specifically, in the present invention, by moving the spot of short pulse laser beams and the substrate on which polymer as the sample, which is the analyzing subject, is coated, ablation to the large number of samples coated across a wide area can be performed without omission/duplication. This is particularly effective in application to the DNA microarray.

In the present invention, due to the above-described characteristics, not only analysis speed becomes remarkably faster than the conventional one but also simultaneous analysis for the expression of gene, whose expression quantity is extremely small, can be performed.

Then, as a specific application example of the present invention, for example, there exists gene expression analysis using the DNA microarray, and it is possible to increase the speed of its analysis. Specifically, according to the present invention, various kinds of isotopes can be used as labels, and when a stable isotope is used as a label, for example, it is possible to increase the kinds of labels to as many as the number of varieties of stable isotopes (270 kinds). As a result, the amount of information can be significantly increased comparing to a fluorescence method (2 to 6 kinds) that is a conventional labeling method and a radioisotope (approximately 10 kinds).

More specifically, as a label used in a DNA microarray experiment, a probe labeled by nucleotide containing stable isotope such as $^{39}K$ and $^{41}K$, which is the stable isotope of group 1 in the periodic table, $^{32}S$ and $^{35}S$, which is the stable isotope of group 16 in the periodic table, $^{35}Cl$ and $^{37}Cl$, which is the stable isotope of group 17 in the periodic table, or $^{118}Sn$ and $^{120}Sn$, which is the transition metal in the periodic table, for example, is used.

After hybridizing the probe with a target nucleic acid on the DNA microarray, ablation is performed by ultra-short pulse laser, atomic ionization is performed to particles, and then the mass spectrograph detects them, for example, and thus it is possible to determine the quantity of the isotope contained in the hybridized probe. Therefore, the quantity ratio of the probe can be found by calculation.

Herein, the probe has been labeled by fluorochrome in a conventional DNA microarray technique. In the conventional method, approximately 10 minutes were required for detection using exclusive detection equipment after hybridization. However, detection speed can be increased when the present invention is used.

Moreover, only two kinds of fluorochrome (Cy-3, Cy-5) are currently used, and it is not expected to rapidly increase. On the other hand, it is possible to increase the kinds of labels to as many as 270 kinds when the stable isotope is used.

Further, the gene expression data of the DNA microarray is obtained as a relative value to a reference sample. In short, it is difficult to compare the data of the large number of samples between experiments in the conventional DNA microarray experiment where only two kinds of fluorescent label can be used.

However, if a plurality of probes (three kinds or more) labeled by different elements are mixed and simultaneously hybridized with the target, and when the multi-channeled DNA microarray that is measured by the method of analyzing polymer of the present invention, which uses laser ablation is used, data of plural samples can be compared.

Consequently, the present invention is one capable of establishing a highly sensitive and high-speed mass analysis by various kinds of stable isotopic tracer, and therefore, the present invention can be applicable to all fields of research, where labeling is performed by fluorochrome or radioisotope.

Further, according to the present invention, since stable isotope can be used for the labeled element without using radioisotope and no restriction is imposed in facility used in this case, installation in medical facilities and private enterprises is made possible, and its spillover effects is unmeasurable.

BRIEF DESCRIPTION OF THE DRAWINGS

FIGS. 3(a), (b) and (c) are mass spectrum of sample 1, which has been measured by a quadrupole mass spectrograph. FIGS. 3(a), (b) and (c) show the case where the output of short pulse laser beams was set to 230 μJ, the case where the output of short pulse laser beams was set to 53 μJ, and the case where the output of short pulse laser beams was set to 48 μJ, respectively. It is to be noted that the measurement in FIG. 3(c) was conducted by reducing the sensitivity of the quadrupole mass spectrograph by two digits comparing to the measurement cases of FIG. 3(a) and FIG. 3(b).

DESCRIPTION OF REFERENCE NUMERALS 10 mass analysis system
12 vacuum chamber
14 target
16 quadrupole mass spectrograph
18 rotational inlet terminal
20 ultra-shot pulse laser
22 focus lens

BEST MODE FOR CARRYING OUT THE INVENTION

In the following, an example of the method of analyzing polymer using laser ablation and system therefor according to the present invention will be described in detail referring to the attached drawings.

Figure 1:
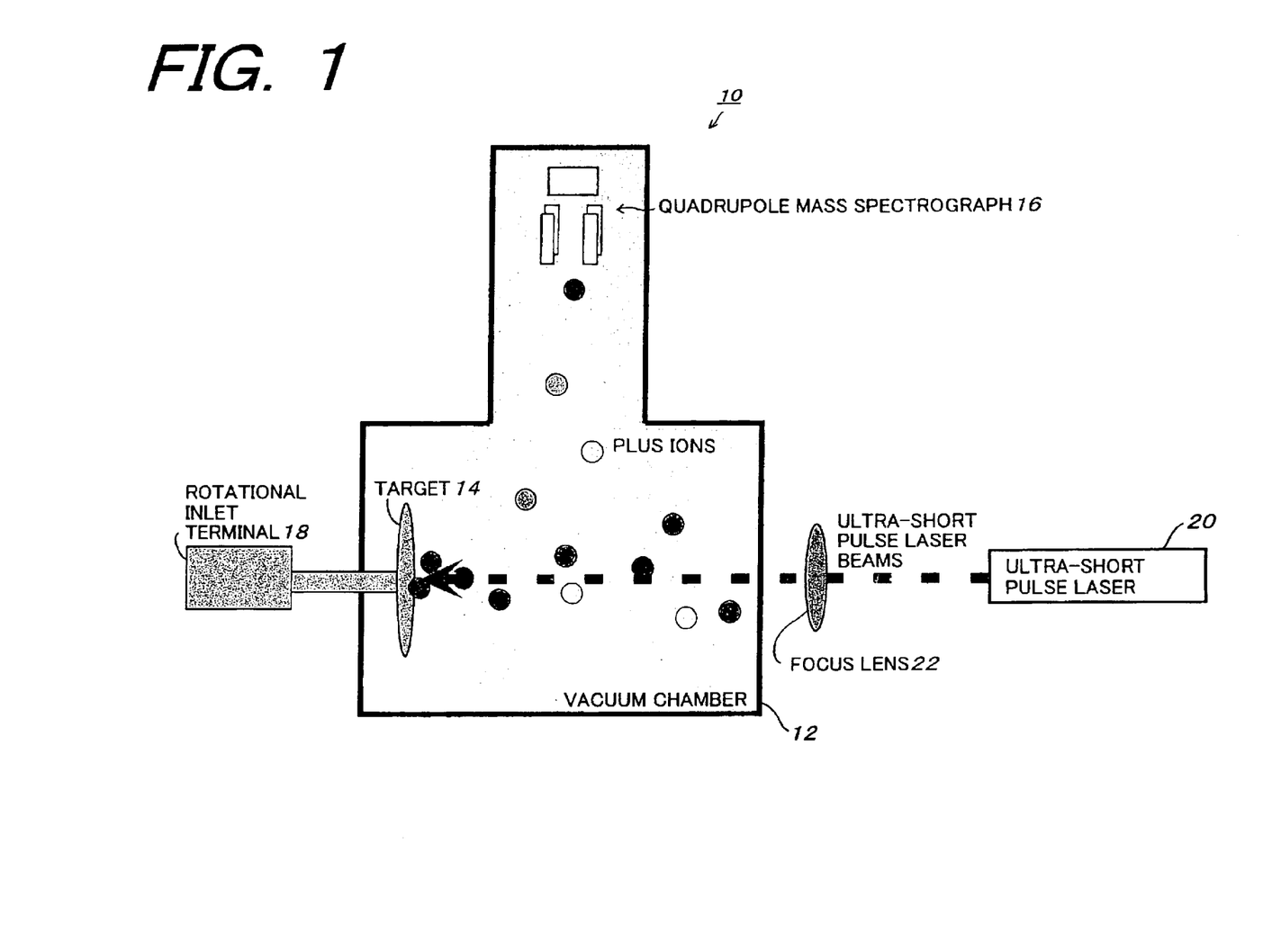
FIG. 1 is a conceptual configuration schematic diagram of an example of the configuration of a mass analysis system that is an example of analysis system for polymer to execute the method of analyzing polymer using laser ablation, according to the present invention.

FIG. 1 shows the conceptual configuration schematic diagram of an example of the configuration of the mass analysis system as an example of the analysis system for polymer to execute the method of analyzing polymer using laser ablation, according to the present invention.

The mass analysis system 10 comprises the vacuum chamber 12 that can be set to the degree of vacuum of $10^{-8}$ to $10^{-6}$ Torr, the target 14 arranged in the vacuum chamber 12, the quadrupole mass spectrograph 16 arranged in the vacuum chamber 12, the rotational inlet terminal 18 that rotates the target 14, the ultra-short pulse laser 20 that emits ultra-short pulse laser beam to irradiate the target 14, and the focus lens 22 that condenses the ultra-short pulse laser beams emitted from the ultra-short pulse laser 20 onto the target 14.

Herein, the ultra-short pulse laser 20 consists of titanium sapphire laser and has parameters as shown below. It is as follows:

Peak width (pulse duration): ~110 fs (femto seconds)
Output: 50~480 $\mu$J (micro Joule)
(Peak power: 0.5~4 GW (gigawatt))
Wavelength: ~800 nm (nanometers)
Repeating frequency: 1 kHz (kilohertz)

It is to be noted that the quadrupole mass spectrograph 16 is installed in a vertical direction by 90 degrees to the irradiation direction of the ultra-short pulse laser beams that is emitted from the ultra-short pulse laser 20 and irradiated on the target 14.

Further, the focal length of the focus lens 22 that condenses the ultra-short pulse laser beams emitted from the ultra-short pulse laser 20 is set to 25 cm, for example.

In the above construction, description will be given for the experimental result through actual mass analysis using the above-described mass analysis system 10.

Figure 2:
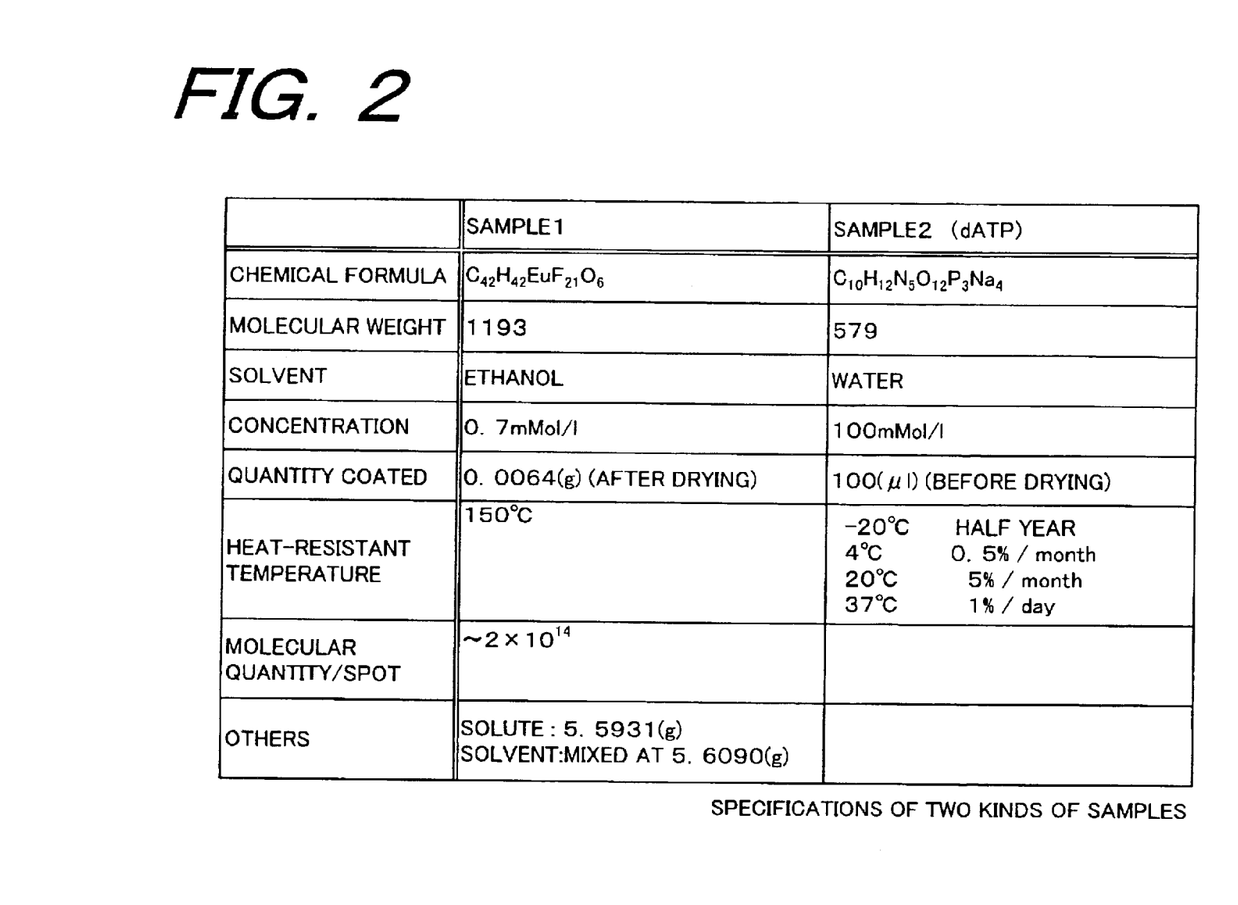
FIG. 2 is a table showing the specifications of two kinds of sample (sample 1 and sample 2) used in experiment.

First, the two kinds of samples (sample 1 and sample 2) having the specifications shown in FIG. 2 were used as the sample for experiment. Then, by using the two kinds of samples, the target 14 was formed by a spin coating method.

Specifically, a silicon substrate of an approximately square shape having 2 cm by one side is prepared, and thick solution of sample 1 or sample 2 is dropped thereon by a dropper. Subsequently, the silicon substrate is made to rotate at 1000 rotations/second for 90 seconds. As a result, the solution of sample 1 or sample 2 evaporates solvent to transform into solid phase as it widens, and cures while it keeps a surface flat. Then, the silicon substrate where sample 1 or sample 2 cured on the surface thereof is further placed in a thermostat of approximately 120 degrees (C.) and is left to stand for 30 minutes to 1 hour.

With this method, it is possible to form the target 14 on which sample 1 or sample 2, which covers the area of 1 cm or more, is formed evenly and with the concentration of approximately $10^{13}$ per spot of one shot of ultra-short pulse laser beams emitted from the ultra-short pulse laser 20.

Herein, the material of the substrate does not need to be semiconductor, but may be metal or insulator. In laser ablation using ultra-short pulse laser beams, a substrate having high thermal conductivity gives higher ion detection efficiency. It is to be noted that a solid is used as the substrate, and it is preferable that the thermal conductivity of the solid used as the substrate is 0.1 $W.m^{-1}.k^{-1}$ or more.

The target 14 formed as described above is installed in the vacuum chamber 14, the inside of the vacuum chamber 12 is vacuumized to set the degree of vacuum inside the vacuum chamber 12 to $10^{-6}$ Torr or less.

Subsequently, the ultra-short pulse laser beams emitted from the ultra-short pulse laser 20 is condensed on to the target 14 using the focus lens 22, and ablation is performed to sample 1 or sample 2 formed on the target 14.

It is to be noted that the pulse width of the ultra-short pulse laser beams emitted from the ultra-short pulse laser 20 is 110 femto seconds, and the output was changed to 53 $\mu$J, 23 $\mu$J and 480 $\mu$J.

Then, the quadrupole mass spectrograph 16 measures the mass of the univalent ions generated by the irradiation of the ultra-short pulse laser beams on the target 14.

Figure 3:
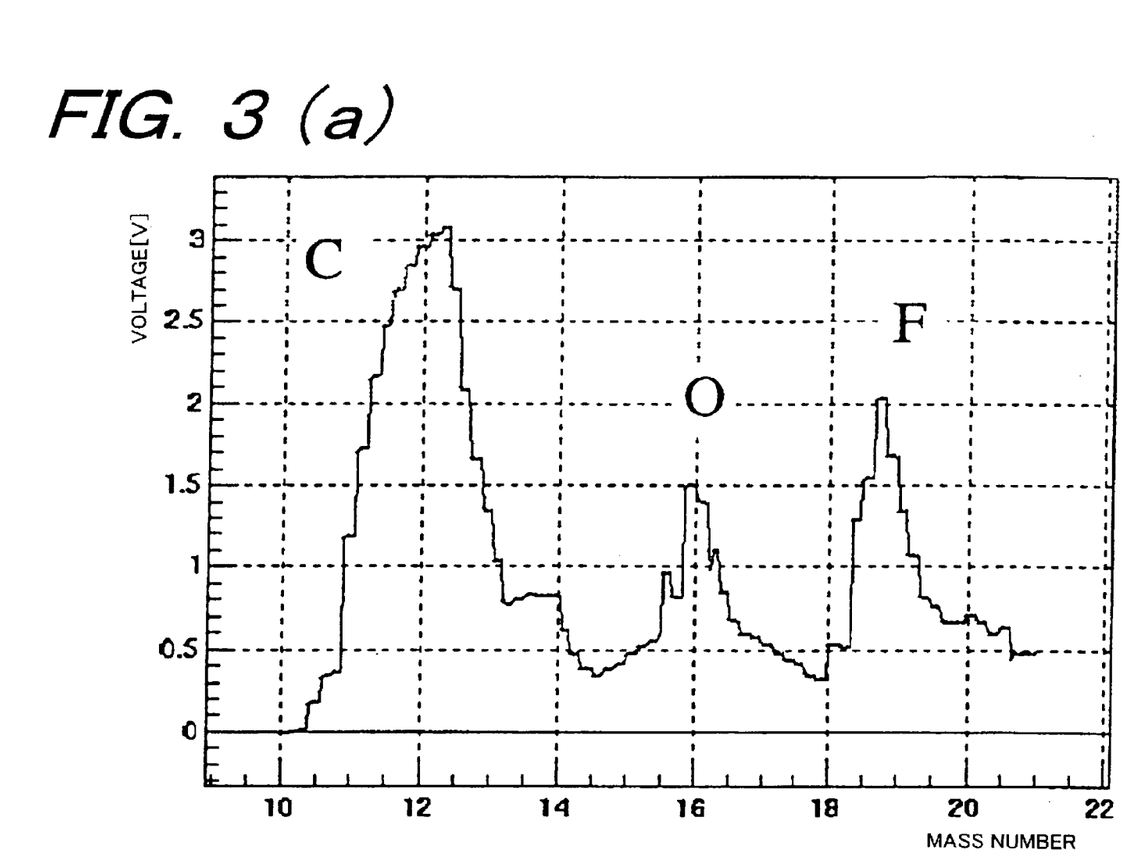
Figure 3C:
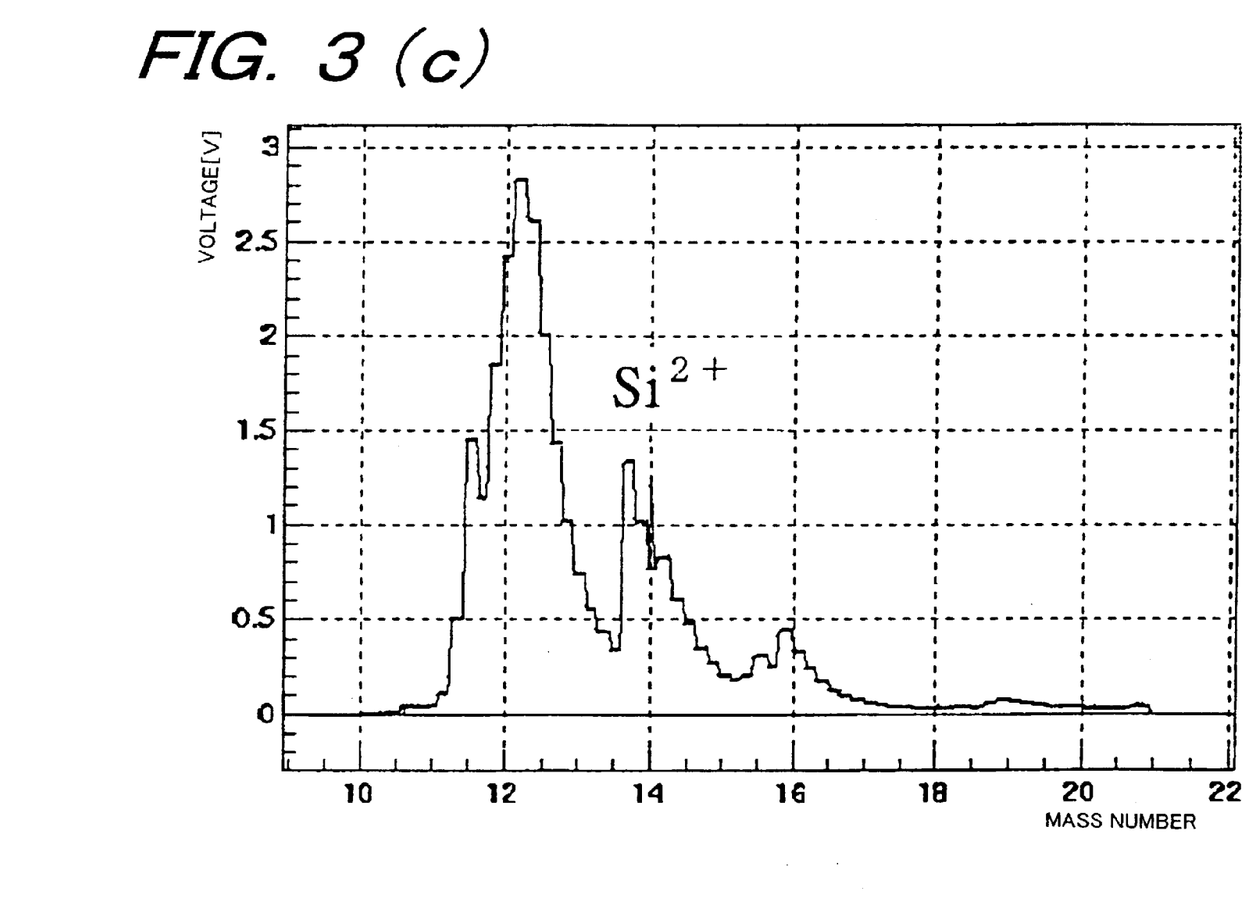

FIGS. 3(a), (b) and (c) show the mass spectrum of sample 1, which was measured by the quadrupole mass spectrograph 16.

By increasing the output of short pulse laser beams from 53 $\mu$J (refer to FIG. 3(b)) to 230 $\mu$J (refer to FIG. 3(a)), it was possible to detect $^{12}C$, $^{16}O$ and $^{19}F$, which became univalent ions, in quantity corresponding to their component ratio.

Consequently, the polymer of sample 1 was atomized by the ablation of the ultra-short pulse laser such as the femto second laser, and it has been confirmed that ionization was also performed simultaneously with the atomization.

Herein, when the output of short pulse laser beams is increased further to 480 $\mu$J, the ratio of C increased and a peak that is considered to be of bivalent silicon ions appeared prominently (refer to FIG. 3(c). It is to be noted that the measurement in FIG. 3(c) was conducted by reducing the sensitivity of the quadrupole mass spectrograph by two digits comparing to the measurement cases of FIG. 3(a) and FIG. 3(b).

Figure 4:
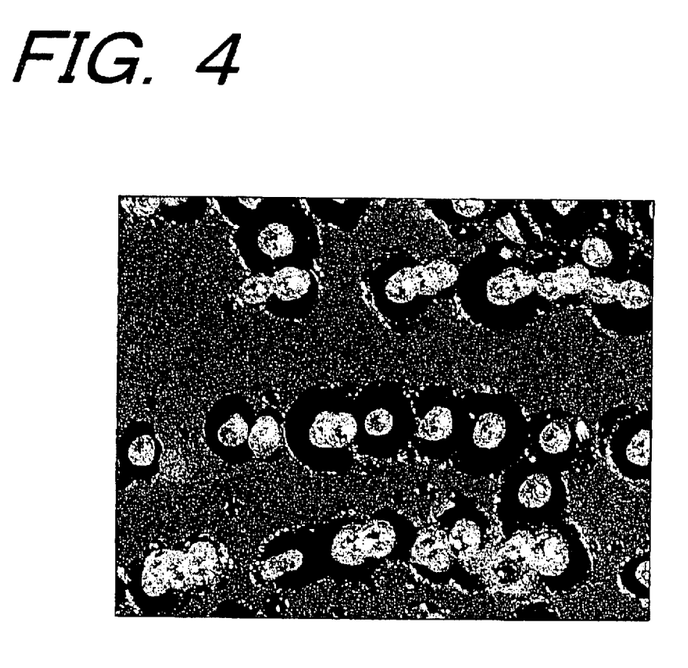
FIG. 4 is a view showing the state where the status of a target, from which sample 1 was peeled off by the irradiation of ultra-short pulse laser beams, has been observed by a microscope.

Next, FIG. 4 shows a micrograph showing the status of the target 14, from which sample 1 was peeled off by the irradiation of ultra-short pulse laser beams. In FIG. 4, concentrically formed double circles, which are inner white circles and outer black circles around them, are visually recognized. The one spot corresponds to the irradiation of 8 ms of the opening time of shutter. In other words, it can be concluded that sample 1 was peeled off by the pulse equivalent to approximately 8 shots of ultra-short pulse laser beams.

Figure 5:
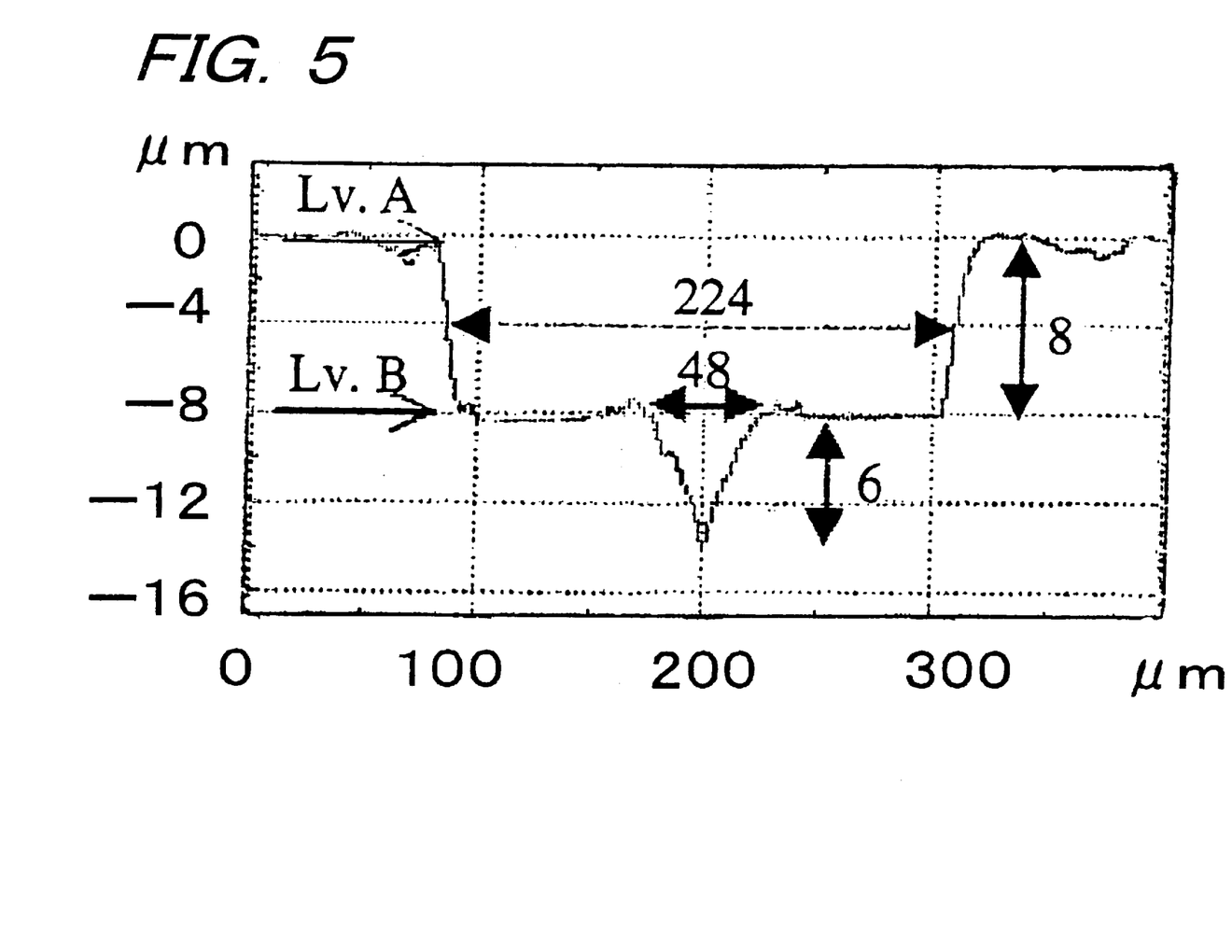
FIG. 5 is an exemplary view showing a measurement result of the depth and the area of a scar formed on the target.

FIG. 5 shows the measurement result of the depth and the area of the scar formed on the target 14. Herein, depth level B (Lv.B) is considered to be the surface of the silicon substrate, and it is recognized that sample 1, which had been in the cylinder of the depth of 8 µm and the width of 224 µm, and silicon in the cone of the depth of 6 µm and the width of 48 µm were peeled off by the pulse equivalent to 8 shots. The following result is obtained when the amount of sample and the amount of silicon, which were peeled off by one shot of ultra-short pulse laser beams, are estimated.

The amount of sample peeled off by one shot of ultra-short pulse laser beams:

$$(224/2)^2 \pi \times 8 \times 10^{-12} [cm^3] \times 1[g/cm^3] \times \{(6.02 \times 10^{23})/1193\} \div 8 = 2.0 \times 10^{13}$$

The amount of silicon peeled off by one shot of ultra-short pulse laser beams:

$$(48/2)^2 \pi \times 6 \times 10^{12} \times (1/3)[cm^3] \times 2.33[g/cm^3] \times \{(6.02 \times 10^{23})/28\} \div 8 = 2.3 \times 10^{13}$$

As described above, it has been proven from the experimental result regarding sample 1 that it was possible to atomize/ionize polymer by the ablation of ultra-short pulse laser beams (specifically, it is the femto second laser beams having the pulse duration of 110 femto seconds).

Next, commercially available DATP was used as sample 2 to conduct experiment on a labeled DNA sample, and the experiment was conducted in the same manner as the case of sample 1.

Figure 6:
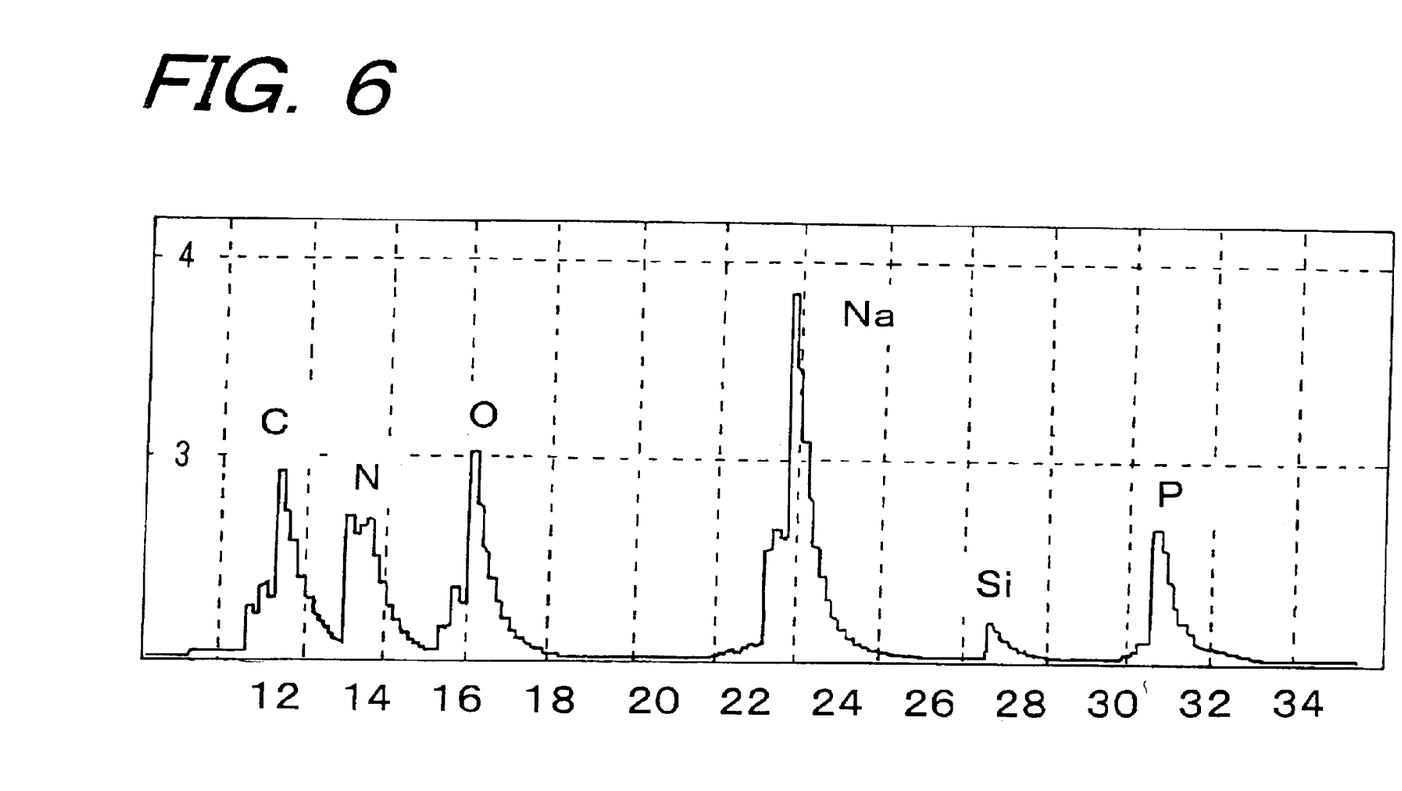
FIG. 6 is the mass spectrum of sample 2, which has been measured by the quadrupole mass spectrograph.

FIG. 6 shows the mass spectrum obtained by the experiment, where it was possible to observe the peaks of $^{12}C$, $^{14}N$, $^{16}O$, $^{23}Na$, and $^{31}P$ of the constituent elements.

From this result, it has been also confirmed that it was possible to atomize/ionize polymer (molecular weight of approximately 500) by the ablation of ultra-short pulse laser beams (specifically, it is the femto second laser beams having the pulse duration of 110 femto seconds). Furthermore, it is also concluded that the isotope of P can be used as a label.

As described above, it has been proven that, by coating polymer on the silicon substrate in high-density, it was possible to atomize/ionize C, N, O, Na, F, P and the like, which are the constituent elements in organic molecules, by the ablation of ultra-short pulse laser beams and, to detect them. Since P in DATP could be detected, the isotope of P can be used as the label.

Next, description will be given for the experimental result when the sample shown below (S-substituted DNA sample as DNA sample having group 16 element) is used as sample 3, and the pulse duration of the ultra-short pulse laser 20 and the peak power are respectively set to 110 femto seconds and 2GW.

Sample 3: 2'-Deoxyadenosine 5'-O-(1-Thiotriphosphate)

Chemical formula: $C_{10}H_{13}N_5O_{11}P_3SNa_3 \cdot 3H_2O$

In the case of sample 3 as well, similar to the case of the experiment regarding sample 1 and sample 2, the target 14 is prepared first, where solution in which polymer being the sample that is the subject of mass analysis (the above-described S-substituted DNA sample) is dissolved is coated on the silicon substrate, the silicon substrate is left to stand in the thermostat of 50 degrees (C.) for approximately 30 minutes, and the solvent coated on the silicon substrate is evaporated, before the mass analysis of polymer by the mass analysis system 10.

The target 14 where sample 3 was cured on the surface thereof as described above is installed in the vacuum chamber 12, the inside of the vacuum chamber 12 is vacuumized to set the degree of vacuum inside the vacuum chamber 12 to $10^{-6}$ Torr or less.

Subsequently, the ultra-short pulse laser beams having the above-described parameters, which are emitted from the ultra-short pulse laser 20, are condensed on to the target 14 using the focus lens 22, and ablation is performed to the target 14.

By rotating the target 14 by the rotational inlet terminal 18, ablation is performed to the target 14 in a spot shape without omission/duplication. Further, during ablation, by opening/closing the shutter while moving the focus lens 22, ablation can be performed to the target 14 in the spot shape without omission/duplication.

Then, the quadrupole mass spectrograph 16 measures the mass of univalent ions generated by the irradiation of ultra-short pulse laser beams to the target 14.

Figure 7:
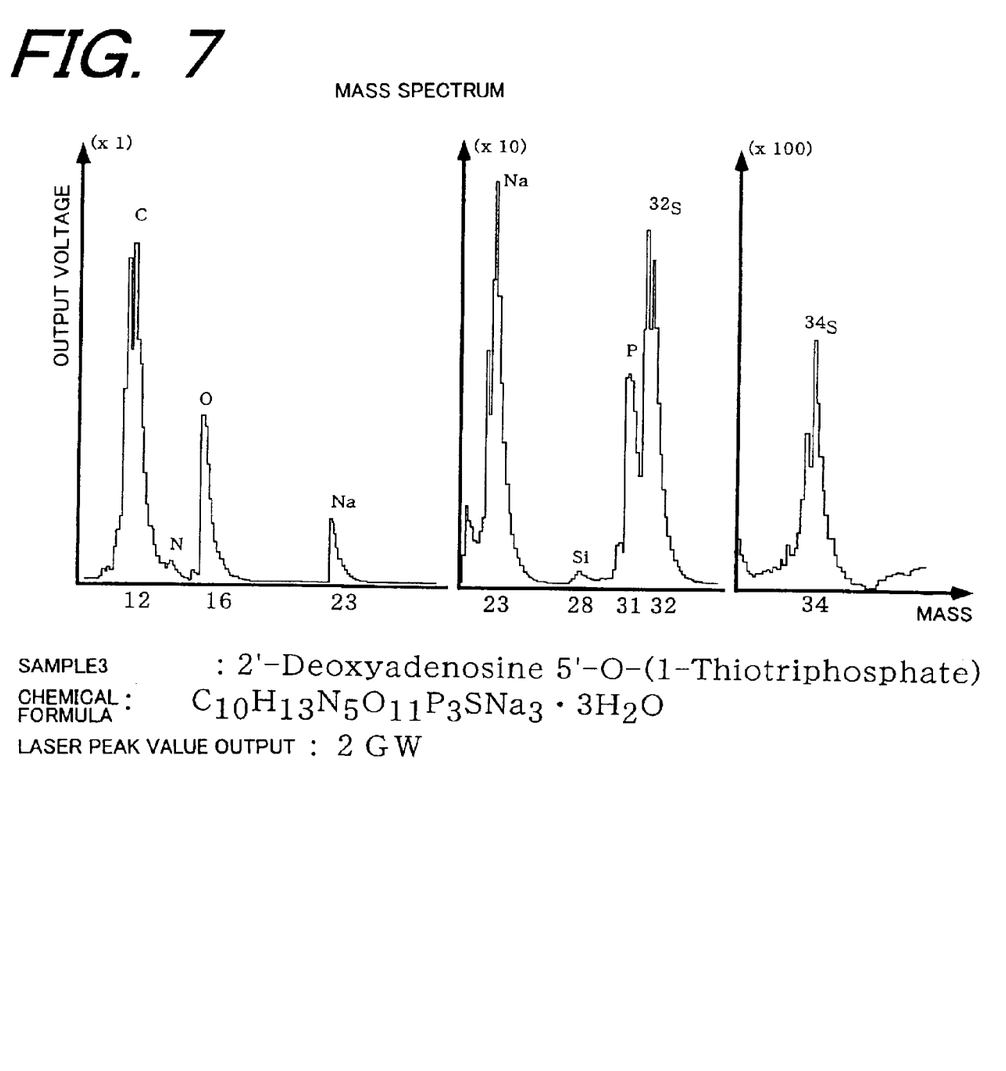
FIG. 7 is the mass spectrum of sample 3, which has been measured by the quadrupole mass spectrograph.

FIG. 7 shows an example of the mass spectrum of a sample, which was measured by the quadrupole mass spectrograph 16 with the above-described method.

Next, description will be given for the experimental result when the sample shown below (Cl-substituted DNA sample as DNA sample having group 17 element) is used as sample 4, and the pulse duration of the ultra-short pulse laser 20 and the peak power are respectively set to 110 femto seconds and 2 GW.

Sample 4: 5-Chloro-2'-Deoxyuridine

Chemical formula: $C_9H_{11}ClN_2O_5$

In the case of sample 4 as well, similar to the case of the experiment regarding sample 1 and sample 2, the target 14 is prepared first, where solution in which polymer being the sample that is the subject of mass analysis (the above-described Cl-substituted DNA sample) is dissolved is coated on the silicon substrate, the silicon substrate is left to stand in the thermostat of 50 degrees (C.) for approximately 30 minutes, and the solvent coated on the silicon substrate is evaporated, before the mass analysis of polymer by the mass analysis system 10.

The target 14 where sample 4 was cured on the surface thereof as described above is installed in the vacuum chamber 12, the inside of the vacuum chamber 12 is vacuumized to set the degree of vacuum inside the vacuum chamber 12 to $10^{-6}$ Torr or less.

Subsequently, the ultra-short pulse laser beams having the above-described parameters, which are emitted from the ultra-short pulse laser 20, are condensed on to the target 14 using the focus lens 22, and ablation is performed to the target 14.

By opening/closing the shutter while moving the focus lens 22, ablation can be performed to the target 14 in the spot shape without omission and duplication.

Then, the quadrupole mass spectrograph 16 measures the mass of univalent ions that was generated by the irradiation of ultra-short pulse laser beams to the target 14.

Figure 8:
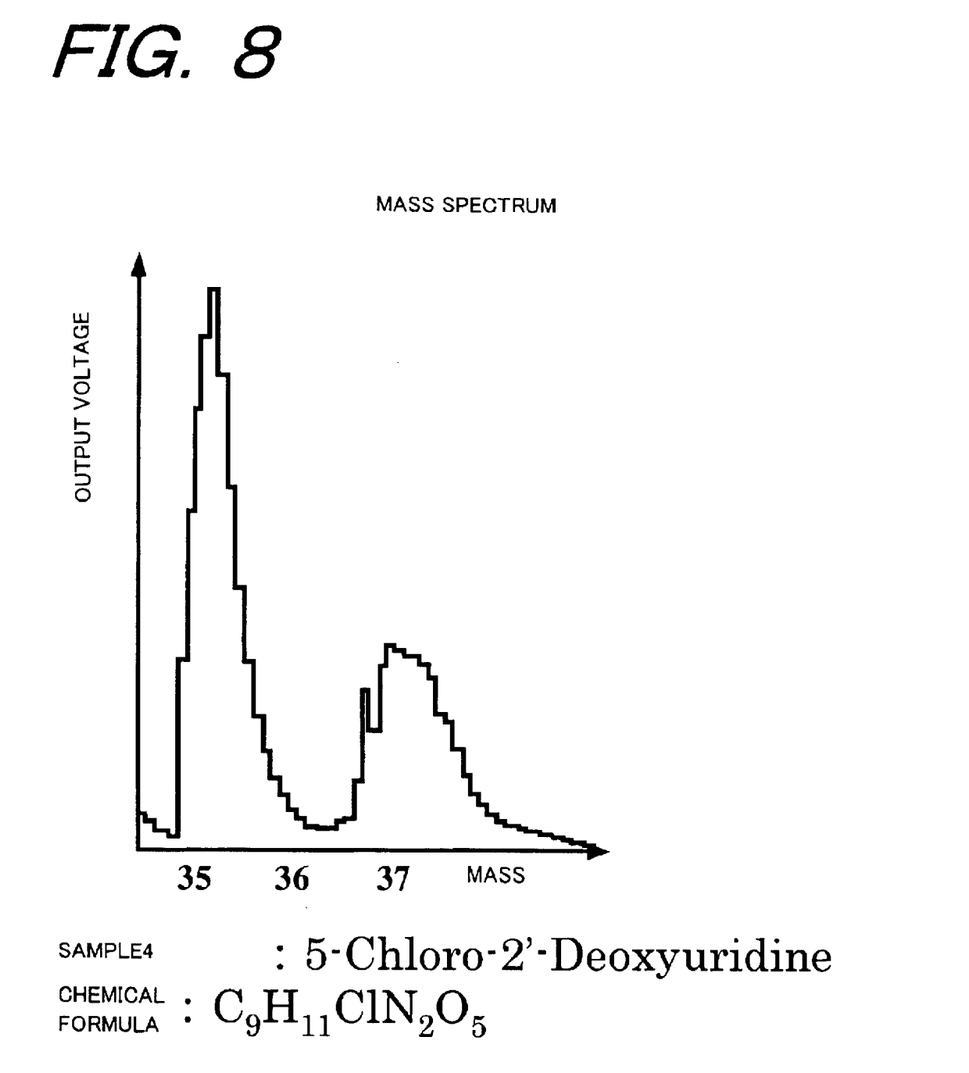
FIG. 8 is the mass spectrum of sample 4, which has been measured by the quadrupole mass spectrograph.

FIG. 8 shows an example of the mass spectrum of a sample, which was measured by the quadrupole mass spectrograph 16 with the above-described method.

It is to be noted that the method of analyzing polymer using laser ablation according to the present invention can be used in mass analysis of various kinds of polymer such as DNA, protein, RNA, PNA, lipid, sugar and the like, for example.

Further, regarding these various kinds of polymer, it is a matter of course that analysis can be conducted to the ones attached with elemental label.

Specifically, by performing ablation by ultra-short pulse laser to polymer such as protein, albumin and DNA, which is labeled by single or plural number of isotope, polymer constituent elements are completely transferred into atomic ions, mass analysis is conducted to the ionized labeled elements, and thus it is possible to determine the quantity of polymer. Consequently, various kinds of isotope can be used as labels. Accordingly, it is possible to dramatically widen the subject range of polymer to which mass analysis can be performed.

In other words, the present invention makes it possible to ionize the polymer sample itself labeled by the isotope on an atomic level and detect the labeled element, so that it is possible to dramatically widen the subject range where mass analysis can be performed. For example, the isotope can be used as the label of DNA, and the kinds of labels can be increased to as many as 270 that is the number of the stable isotopes. The amount of information can be significantly increased comparing to the fluorescence method (2 kinds) that is the conventional labeling method and the radioisotope (approximately 10 kinds).

It is to be noted that the quadrupole mass spectrograph was used as a mass spectrograph in the above-described embodiments, but it is needless to say that the invention is not limited to this, and mass analysis of plural numbers of atoms can be simultaneously performed by one laser irradiation when a time-of-flight mass spectrograph, that performs mass analysis by measuring the time of flight of atoms, is used. Further, the mass analysis of plural numbers of atoms can be simultaneously performed as well when the Fourier transform mass spectrograph of ion cyclotron type is used as the mass spectrograph.

Furthermore, description was given for the mass analysis as the method of analyzing polymer in the above-described embodiments, but it is needless to say that the invention is not limited to this, and the present invention may be used for analysis other than mass analysis.

Moreover, although the above-described embodiments used the rotational inlet terminal 18 that rotates the target 14 as the moving means for moving the target, it is a matter of course that the invention is not limited to this, and appropriate moving means such as a freely movable table capable of mounting the target 14 may be used.

In addition, in the above-described embodiments, although ablation was performed to the target 14 without omission/duplication by rotating the target 14 using the rotational inlet terminal 18, it is a matter of course that the invention is not limited to this, and ablation may be performed to the target 14 without omission/duplication by providing moving means that moves the irradiation position of ultra-short pulse laser beams to the target.

INDUSTRIAL APPLICABILITY

Since the present invention is constructed as described above, it is the method of analyzing polymer using laser ablation and the system therefor, where the atomic ions of the constituent elements that constitute the polymer are generated, and the generated atomic ions are analyzed. It exerts superior effects that the invention is capable of providing the method of analyzing polymer using laser ablation, in which a spectrograph having high resolving power is not required, and the system therefor. Herein, in more detail, the invention exerts superior effects that it eliminates a chance where the analysis of mass spectrum becomes difficult and the mass spectrograph having high resolving power is not required, in the case of performing mass analysis.

Further, since the present invention is constructed as described above, it exerts superior effects that the system construction can be dramatically simplified.

Furthermore, since the present invention is constituted as described above, it exerts superior effects that efficient analysis can be performed even in the state where various kinds of labeled isotopes are mixed.

What is claimed is:

1. A method of analyzing polymer using laser ablation, where polymer is atomized into constituent elements by irradiating laser beams on the polymer, which is an analyzing subject, to perform ablation to the polymer, the atomized constituent elements are ionized, and the ionized constituent elements are analyzed, wherein the laser beams irradiated on the polymer, which is the analyzing subject, to perform ablation to the polymer are ultra-short pulse laser beams, and the polymer is simultaneously atomized into constituent elements and ionized by irradiating the ultra-short pulse laser beams on the polymer, which is the analyzing subject, to perform ablation to the polymer, and the ionized constituent elements are analyzed.

2. A method of analyzing polymer using laser ablation as claimed in claim 1, wherein the polymer, which is the analyzing subject, is transformed into solid phase.

3. A method of analyzing polymer using laser ablation as claimed in claim 2, wherein a method of transforming polymer into solid phase is a method that includes a process of transforming the polymer into solid phase by dropping solution of the polymer, which is the analyzing subject, onto a substrate to dry.

4. A method of analyzing polymer using laser ablation as claimed in claim 3, wherein said substrate is a solid and the thermal conductivity of the solid is 0.1 $W.m^{-1}.K^{-1}$ or more.

5. A method of analyzing polymer using laser ablation as claimed in claim 1, wherein the polymer that is the analyzing subject is added with an elemental label.

6. A method of analyzing polymer using laser ablation as claimed in claim 5, wherein said elemental label is a group 1 element in the periodic table.

7. A method of analyzing polymer using laser ablation as claimed in claim 5, wherein said elemental label is a group 16 element in the periodic table.

8. A method of analyzing polymer using laser ablation as claimed in claim 5, wherein said elemental label is a group 17 element in the periodic table.

9. A method of analyzing polymer using laser ablation as claimed in claim 5, wherein said elemental label is a transition metal element in the periodic table.

10. A method of analyzing polymer using laser ablation as claimed in claim 5, wherein said elemental label is a stable isotopic label.

11. A method of analyzing polymer using laser ablation as claimed in any one of claims 1 to 10, wherein the ultra-short pulse laser beams irradiated on the polymer, which is the analyzing subject, to perform ablation to the polymer have a pulse duration of 10 pico seconds or less and a peak power of 10 megawatt or more.

12. A method of analyzing polymer using laser ablation as claimed in claim 11, wherein the ultra-short pulse laser beams irradiated on the polymer, which is the analyzing subject, to perform ablation to the polymer have the pulse duration of 1 femto second or more and 1 pico second or less, and the peak power of 1 gigawatt or more and 10 gigawatt or less.

13. A method of analyzing polymer using laser ablation as claimed in claim 1, wherein the analysis of said ionized constituent element is mass analysis.

14. A method of analyzing polymer using laser ablation as claimed in claim 13, wherein the mass analysis is mass analysis by a time-of-flight method.

15. A method of analyzing polymer using laser ablation as claimed in claimed in claim 1, wherein said method simultaneously analyzes a plurality of ionized constituent elements.

16. A method of analyzing polymer using laser ablation as claimed in claim 1, wherein the polymer that is the analyzing subject is nucleic acid or the analog of nucleic acid, which is fixed on a DNA microarray.

17. A method of analyzing polymer using laser ablation as claimed in claim 16, wherein said DNA microarray is a multi-channel DNA microarray.

18. A method of analyzing polymer using laser ablation as claimed in claim 1, wherein by moving at least either one of short pulse laser beams that perform ablation to polymer and the polymer that is the analyzing subject, the short pulse laser beams that perform ablation to the polymer perform ablation to the polymer, which is the analyzing subject, without omission and duplication.

19. An analysis system for polymer using laser ablation, where polymer is atomized into constituent elements by irradiating laser beams on the polymer, which is the analyzing subject, to perform ablation to the polymer, the atomized constituent elements are ionized, and the ionized constituent elements are analyzed, said system comprising:

a vacuum chamber capable of arranging a target inside thereof;

a spectrograph arranged in said vacuum chamber; and an ultra-short pulse laser that emits ultra-short pulse laser beams to irradiate the target arranged in said vacuum chamber.

20. An analysis system for polymer as claimed in claim 19, further comprising:

moving means that moves the target in said vacuum chamber.

21. An analysis system for polymer as claimed in claim 20, wherein said moving means that moves said target is rotational means that rotates the target.

22. An analysis system for polymer as claimed in claim 19, further comprising:

moving means that moves the irradiation position of the ultra-short pulse laser beams to the target.

23. An analysis system for polymer as claimed in any one of claims 19 to 22, wherein said spectrograph is a mass spectrograph.

24. An analysis system for polymer as claimed in claim 23, wherein said mass spectrograph is a quadrupole mass spectrograph.

25. An analysis system for polymer as claimed in claim 23, wherein said mass spectrograph is a time-of-flight mass spectrograph.

26. An analysis system for polymer as claimed in claim 23, wherein said mass spectrograph is a Fourier transform mass spectrograph of ion cyclotron type.

27. An analysis system for polymer as claimed in claim 19, wherein said ultra-short pulse laser irradiates short pulse laser beams having a pulse duration of 10 pico seconds or less and a peak power of 10 megawatt or more.

28. An analysis system for polymer as claimed in claim 27, wherein said ultra-short pulse laser irradiates short pulse laser beams having the pulse duration of 1 femto second or more and 1 pico second or less and the peak power of 1 gigawatt or more and 10 gigawatt or less.

* * * * *